United States Patent [19]

Vidra et al.

[11] 3,991,177

[45] Nov. 9, 1976

[54] ORAL COMPOSITIONS CONTAINING DEXTRANASE

[75] Inventors: James David Vidra, Clinton; Julius Harvey Nachtigal, Colonia, both of N.J.

[73] Assignee: Colgate-Palmolive Company, New York, N.Y.

[22] Filed: Mar. 12, 1975

[21] Appl. No.: 557,855

Related U.S. Application Data

[63] Continuation-in-part of Ser. No. 419,343, Nov. 27, 1973, abandoned, which is a continuation-in-part of Ser. No. 313,304, Dec. 8, 1972, abandoned.

[52] U.S. Cl. .................................. 424/50; 424/94
[51] Int. Cl.$^2$ .......................................... A61K 7/28
[58] Field of Search ............................. 424/49–58, 424/94

[56] References Cited
UNITED STATES PATENTS

| | | | |
|---|---|---|---|
| 1,817,664 | 8/1931 | Badanes | 424/49 |
| 3,622,661 | 11/1971 | King et al. | 424/50 |
| 3,686,393 | 8/1972 | Woodruff et al. | 424/50 |
| 3,737,383 | 5/1973 | Abe et al. | 424/50 |

FOREIGN PATENTS OR APPLICATIONS 2,358,217  6/1974  Germany

OTHER PUBLICATIONS

Manly et al., *J. Dental Research*, vol. 28, No. 2, p. 167, 1949.
Goudot, Chem. Abstr., 52, No. 2514b (1958).
Shkolnik et al., Chem. Abstr. 65, No. 2559c (1966).
Byalik, Chem. Abstr., 70, No. 763459 (1969).
Byalik, Chem. Abstr., 69, No. 66030r (1968).
Koenig, Chem. Abstr., 70, No. 75838h (1969).

*Primary Examiner*—Shep K. Rose
*Attorney, Agent, or Firm*—Robert L. Stone; Murray M. Grill; Herbert S. Sylvester

[57] ABSTRACT

Oral compositions containing dextranase and a stabilizer/activator selected from the group consisting of manganeous ions, calcium ions, and mixtures thereof.

4 Claims, No Drawings

ORAL COMPOSITIONS CONTAINING DEXTRANASE

This application is a continuation-in-part of Ser. No. 419,343, abandoned, filed Nov. 27, 1973, which is a continuation-in-part of Ser. No. 313,304, filed Dec. 8, 1972, now abandoned.

This invention relates to oral compositions containing dextranase and to their method of preparation. The oral compositions of this invention are characterized by their stability and increased activity. This stability and increased activity are due to the presence of specific metal ions.

Dextranase has been proposed to be an effective caries-preventive agent useful in the removal of bacteria on dextran-containing plaque. One of the major deterrents to the use of dextranase in oral compositions has been the inability to formulate a liquid carrier which would maintain the enzyme in an active state. Unfortunately, when dextranase is incorporated into aqueous solution, enzyme inactivation occurs and dextranase is broken down and thereby deactivated to such a degree that its effectiveness is lost.

Accordingly, it is an object of this invention to provide a stabilized oral composition containing dextranase in a liquid vehicle.

It is another advantage of this invention to provide an oral composition containing dextranase which has increased activity.

Other advantages of this invention will be apparent from consideration of the following description.

In accordance with certain of its aspects, this invention relates to oral preparations comprising a liquid vehicle, dextranase, and a stabilizer/activator selected from the group consisting of manganeous ions, calcium ions, magnesium ions, and mixtures thereof.

The oral compositions of this invention are typically a toothpaste, that is, a dental cream or gel. Such a cream or gel may be employed as a toothpaste or mouth rinse. Generally the compositions also contain a polishing agent, but if the composition is to be used specifically as a mouth rinse, then the polishing agent may be omitted.

Dextranase enzymes are produced from a variety of sources all of which are useful in the present invention. Dextranase enzymes are commonly produced by growing *Penicillium funiculosium* or other fungal sources in a dextran-containing medium. The dextran is commonly a commercial grade obtained from *Leuconostoc mesenterioides*. This commercial grade of dextran contains about 95-percent-α-1,6-glucoside linkages and about 5-percent-α-1,3-glucoside linkages. The Penicillium organism produces the dextranase which particularly hydrolyzes the 1,6-linkages.

Dextranase may also be prepared in accordance with procedures which are described in the art. These include the procedure described by Bowen, "British Dental Journal", Vol. 124, No. 8, dated Apr. 16, 1968, pages 343–349. A further procedure is described in U.S. Pat. No. 2,742,399 to Tsuchiya et al. (Note also Tsuchiya et al., "Journal of Bacteriology", Vol. 64, page 513).

In the procedure of Bowen, dextran may be prepared from noncariogenic streptococcal strains such as ATCC 10558, 903–1600, IIA2+3, or *Leuconostoc mesenterioides* and purified according to the method described by Wood et al., "Archives of Oral Biology", Vol. 11, 1066, pages 1039 et seq., except that *L. mesenterioides* is grown at 25° C.

Dextranase may be prepared from dextran by inoculating *Penicillium funicolosum* into flasks containing 250 ml. of a medium containing 0.5-percent yeast extract and 1-percent dextran. The flasks are incubated at 30° C. on a shaking incubator for 4 days. The culture in then centrifuged at 3,000 g. for 20 minutes and filtered through Whatman 42 filter paper. Dialysis in 16 mm. "Visking" tubing against deionized water and concentrating fifty fold by dialysis against polyethylene glycol (molecular weight 20,000) follows. The dextranase produced in accordance with this procedure has a molecular weight of about 200,000 to 275,000. If desired, the dextranase may be further purified by fractionation with ammonium sulfate.

Additional procedures for preparing dextranase include that described in U.S. Pat. No. 2,742,399 to Tsuchiya et al.

Dextranases of bacterial origin are also useful the present compositions. Bacterial-origin dextranase may be prepared in the general manner in which enzymes are derived from bacteria. However, the preferred source of dextranase for the purposes of this invention is a mutan of *Bacillus coaguluns*, NRRL B-3977 (Beckman dextranase catalogue No. 680000). Bacterial-origin dextranase may be obtained by the addition of α-1,3-dextran or a mixture of α-1,6-, α-1,3-, and α-1,4-dextrans. The bacterial strain may be innoculated into a shaker flask or fermentator for a period of 1 to 5 days at 25° to 40° C. The sterile growth medias can consist of the aforementioned dextran or mutan combined with a mixture of carbohydrate (starch, glucose, sucrose, cellulose), nitrogeneous compounds (protein digest, gelatin, casein, ammonium salts), growth stimulators, (yeast extract, corn steep liquor, distiller's solubles), or minerals. Preservatives may be added and the enzyme decanted, filtered, or centrifuged to precipitate the cells (intracellular dextranase). The extracellular dextranase can be precipitated with ammonium sulfate, acetone, sodium sulfate, or a similar salt. The intracellular dextranases are autolyzed and extracted. Following the salt fractionation step, the enzyme can be further purified by a variety of column (DEAE, Sephodex, ECTEOLA, hydroxyapatite) chromatography methods and frozen or stabilized by the addition of protein, dextran, salt, etc. (The purification steps are usually conducted at refrigerated temperatures.)

The amount of dextranase employed in the oral compositions of the invention is at least such amount as is effective in promoting oral hygiene. This amount is dependent upon the activity of the dextranase which may typically range from 20 to 400 units/mg. protein (protein determined by the Lowry method) and therefore upon the mode of its preparation. A typically prepared dextranase enzyme material has an activity of about 117 units/mg. protein. One Beckman dextranase unit is the amount of enzyme which produces 1.0 M of reducing sugar from "native" dextran per minute at 35° C. and pH 6.0.

While smaller amounts of dextranase may be used, dextranase having an activity of about 20 to 400 units/mg. protein may be present in amounts of about 0.001 to 5 percent by weight of the oral composition, while dextranase having an activity of about 90 or 100 to 150 units/mg protein may be preferably present in amounts of about 0.01 to 0.2 percent by weight.

The stabilizer/activator of the instant invention is a metal ion such as manganese, calcium, magnesium, and mixtures thereof. These ions may be provided by any suitable source. Typical sources include the nontoxic water-soluble salts, e.g. chlorides, sulfates, and nitrates. The most preferred sources being manganeous chloride, calcium chloride, and magnesium chloride.

The stabilizer/activator metal ion is typically employed in an amount of about 0.001 to about 0.3 percent by weight, preferably about 0.1 to 0.3 percent and most preferably about 0.2 to 0.25 percent of the oral composition, unless the composition in a mouth rinse concentrate having an amount generally about 4 times as great to provide for a 3 to 1 dilution.

For optimum conditions, the stabilizer/activator is added to the dextranase, and the combination is incubated for 1 hour at 37° C. before addition to the formulation. The dextranase activity can be measured by a number of art recognized assay methods, but for our purposes the reducing sugar assay is used (Noeling and Bernfield, *Helv. Chim. Acta.*, Vol. 31, page 286, 1948).

The desirable character of the oral compositions of this invention is attained by proportioning cosmetically acceptable and nontoxic aqueous liquid ingredients with solid ingredients to produce an acceptable carrier material. In general, the liquids in the composition will comprise chiefly water, glycerine, aqueous solutions of sorbitol, propylene glycol, polyethylene glycol 400, etc., and suitable mixtures thereof. It is advantageous usually to use a mixture of both water and humectant such as glycerine or sorbitol. The total liquid vehicle content will generally be about 20 to 75 percent by weight of the formulation of which water may constitute up to 20 percent, preferably up to 15 percent, of the formulation.

Toothpaste compositions of this invention form creamy or gel masses of desired consistency which are easily extrudable from a pressurized container or a collapsible aluminum or lead tube.

It is generally preferred to use a binding agent in toothpaste. However, certain synthetic binding agents are incompatible with certain types of dextranases. If the dextranase used is of a fungal origin, the preferred binding agents are Irish moss and gum tragacanth. However, if the dextranase used is of a bacterial origin, then the preferred binding agents are carboxymethylcellulose, hydroxypropylcellulose, and hydroxyethylcellulose. Other conventional binding agents are also compatible with bacterial-origin dextranase, for example, Irish moss, gum tragacanth, and gum karaya.

The binder materials is typically employed in amount of up to about 10% by weight, preferably up to about 5% and most preferably about 0.2-1.5% of the oral composition.

Preferably the oral composition is a dental cream or gel and contains a suitable substantially water-insoluble polishing agent which is compatible with the formulation. Particularly compatible materials include, for example, dicalcium phosphate dihydrate, dicalcium phosphate anhydrous, tricalcium phosphate, magnesium carbonate, calcium sulfate, bentonite, etc., and suitable mixtures thereof. Abrasive resinous substances such as the condensation products of melamine and urea with formaldehyde can also be used. It is preferred to use dicalcium phosphate dihydrate, dicalcium phosphate anhydrous, and calcium carbonate. The polishing agent content is variable, but will generally be up to about 75 percent by weight of the total formulation, typically about 20 to 75 percent.

It is often desirable to include a compatible organic surface-active agent to achieve increased prophylactic action, assist in achieving thorough and complete dispersion of the instant composition throughout the oral cavity, and render the instant compositions more cosmetically acceptable. However, many surface-active agents have been found to deactivate dextranase. One particular class of detergents has been found to be particularly compatible with dextranase is the N-substituted lower alkyl $C_{12}$—$C_{18}$ fatty acid sulfoacetamides. The most preferred surface-active agent of this class is N-2-ethyl laurate potassium sulfoacetamide,

This class of surface-active agents has been found to be compatible with dextranase. In addition to the aforementioned detergent, the sodium, potassium, and ethanolamine salts of N-lauroyl, N-myristoyl, and N-palmitoyl sarcosinates are also compatible with dextranase.

Other suitable surface-active agents include compatible nonionic surface-active agents, such as condensates of sorbitan monostearate with approximately 60 moles of ethylene oxide, and condensates of ethylene oxide with propylene oxide condensates of propylene glycol ("Pluronics").

It is preferred to use from about 0.05 to 5 percent by weight of the foregoing surface-active agents in the instant compositions.

Various other materials may also be incorporated into the carrier. Examples thereof are coloring or whitening agents (for example, titanium dioxide), preservatives (for example, sodium benzoate), silicones, chlorophyll compounds, ammoniated materials such as urea, diammonium phosphate, and mixtures thereof, alcohol, menthol, and other constituents. These adjuvants are incorporated into the instant compositions in amounts which do not substantially adversely affect the properties and characteristics of the compositions. These adjuvants are suitably selected and used in proper amounts depending upon the particular type of preparation involved.

Additionally, compatible antibacterial agents may be incorporated in the compositions of the invention. Conventional agents include:

$N^1$-(4-chlorobenzyl)-$N^5$-(2,4-dichlorobenzyl)biguanide;
p-chlorophenyl biguanide;
4-chlorobenzylhydryl biguanide;
4-chlorobenzhydrylguanylurea;
N-3-lauroxypropyl-$N^5$-p-chlorobenzylbiguanide;
1,6-di-p-chlorophenylbiguanidohexane;
1-(lauryldimethylammonium)-8-(p-chlorobenzyldimethylammonium)octane dichloride;
5,6-dichloro-2-guanidinobenzimidazole;
$N^1$-p-chlorophenyl-$N^5$-laurylbiguanide;
5-amino-1,3-bis(2-ethylhexyl)-5-methylhexahydropyrimidine;
2,2'dihydroxy-3,5,6,3',5',6'hexachlorodiphenylmethane;
2,2'dihydroxy-5,5'dichlorodiphenylmethane;
and their nontoxic acid addition salts. These agents may be employed in amounts ranging from 0.01 to 5 percent and preferably 0.05 to 1.0 percent.

Any suitable flavoring or sweetening agent may be employed in formulating a flavor for the compositions of the present invention. Examples of suitable flavoring constituents include the flavoring oils, for example, oils of spearmint, peppermint, wintergreen, sassafras, clove, sage, eucalyptus, marjoram, cinnamon, lemon, and orange, as well as methyl salicylate. Suitable sweetening agents include sucrose, lactose, maltose, sorbitol, sodium cyclamate, and saccharine. Suitably, flavor and sweetening agent may together comprise from about 0.01 to 5 percent or more of the compositions of the instant invention.

The oral compositions of the invention may also desirably contain a fluorine-providing compound.

Examples of suitable fluorine-providing compounds include sodium fluoride, stannous fluoride, potassium fluoride, potassium stannous fluoride ($SnF_2KF$), sodium hexafluorostannate, stannous chlorofluoride, sodium fluorozirconate, and sodium monofluorophosphate. These materials, which dissociate or release fluorine containing ions in water, suitably are present in an effective but nontoxic amount, usually within the range to provide about 0.01 to 1 percent by weight of fluorine, preferably about 0.1 percent.

The instant compositions normally have a pH between about 6.0 and 8.0 and preferably about 6.0. Suitably a buffering system may be employed to assure maintenance of a pH within the aforesaid range.

In order to determine the increase in dextranase activity due to the presence of the metal ions of the instant invention, the following experiment was conducted in which a dextranase control is compared with mixtures of dextranase and the various metal ions.

To prepare the control 0.5 ml. of a 0.067M phosphate buffer (pH 6.0) which contains 5μg. dextranase per 10μl. phosphate buffer is admixed with 1.5 mls. phosphate buffer and 2 mls. 2-percent *Leuconostoc mesenterioides* dextran. The control is incubated at 40° C. for 45 minutes. In preparing the mixtures containing the metal ions the amount of phosphate buffer is adjusted so that the final volume of all mixtures is 4 mls. The dextranase activity is measured by the reducing sugar assay (Noeling and Bernfield).

The results of these experiments are seen in the following table:

| Compositions | Ratio Dextranase to Phosphate Buffer | Amount of 0.067M Phosphate Buffer | Amount of Metal Ion | Amount of Additional 0.067 M Phosphate Buffer |
|---|---|---|---|---|
| Dextranase (Control) | 5μg/10μl | 0.5 ml. | — | 1.5 mls. |
| Dextranase + $Ca^{++}$ | | | 25μl of $2 \times 10^{-2}$ $MCaCl_2$ | 1.475 mls. |
| Dextranase + $Mg^{++}$ | | | 25μl of $2 \times 10^{-2} MMgCl_2$ | 1.475 mls. |
| Dextranase + $Mn^{++}$ | | | 25μl of $2 \times 10^{-2} MMnCl_2$ | 1.475 mls. |
| Dextranase + $Ca^{++}$ + $Mn^{++}$ | | | 25μl of $2 \times 10^{-2} MCaCl_2$ 25μl of $2 \times 10^{-2} MMnCl_2$ | 1.45 mls. |
| Dextranase + $Ca^{++}$ + $Mg^{++}$ | | | 25μl of $2 \times 10^{-2} MCaCl_2$ 25μl of $2 \times 10^{-2} MMgCl_2$ | 1.45 mls. |
| Dextranase + $Mn^{++}$ + $Mg^{++}$ | | | 25μl of $2 \times 10^{-2} MMnCl_2$ 25μl of $2 \times 10^{-2} MMgCl_2$ | 1.45 mls. |
| Dextranase + $Ca^{++}$ + $Mg^{++}$ + $Mn^{++}$ | | | 25μl of $2 \times 10^{-2} MCaCl_2$ 25μl of $2 \times {}^{-2} MMgCl_2$ 25μl of $2 \times 10^{-2} MMnCl_2$ | 1.425 mls. |

$[CaCl_2] = 2 \times 10^{-2}M = 29.4$ mg./10ml. $PO_4$ buffer
$[MnCl_2] = 2 \times 10^{-2}M = 39.6$ mg./10ml. $PO_4$ buffer
$[MgCl_2] = 2 \times 10^{-2}M = 40.6$ mg./10ml. $PO_4$ buffer Dextranase is Beckman Corporation Dextranase (Catalogue No. 680000, activity 117 units/mg. protein)
DNSA is dinitrosalicyclic acid
2% Dextran = 2% Leuconostoc mesenterioides Dextran (M.W. = $5 - 40 \times 10^6$)

| Amount of 2-% Dextran | | Amount DNSA | | Amount Water | Percent Activity Relative to Control |
|---|---|---|---|---|---|
| 2.0 mls. | | 2.0 mls. | | 25 mls. | 100% |
| | | | | | 745% |
| | Add Enzyme Here | | Mix and Δ | | 584% |
| | | | | | 1100% |
| | Incubate at 40° C. | | to boiling; | | 1375% |
| | | | | | 480% |
| | for 45 minutes | | Cool in ice | | 1220% |

As can be seen from the table the presence of the metal ion increases the dextranase activity by quite significant amounts of from about 5 to 14 times that of the control.

In order to determine the stabilizing effect of these metal ions on dextranase, the following toothpaste compositions were formulated and tested over a 9-week aging period.

| Components | EXAMPLE 1 Percent by Weight | EXAMPLE 2 Percent by Weight |
| --- | --- | --- |
| Glycerine | 28.37 | 28.37 |
| Sodium saccharin | 0.20 | 0.20 |
| Sodium benzoate | 0.50 | 0.50 |
| Carboxymethylcellulose | 0.80 | 0.80 |
| Water (Deionized) | 15.38 | 15.18 |
| Calcium carbonate | 5.00 | 5.00 |
| Dicalcium phosphate dihydrate | 46.75 | 46.75 |
| N-2-ethyl laurate potassium sulfoacetamide | 2.00 | 2.00 |
| Flavor | 0.80 | 0.80 |
| Detranase (Beckman, activity 117 units/mg. protein) | 0.20 | 0.20 |
| Manganese chloride tetrahydrate | — | 0.20 |

The results are as follows:

| | Example 1 | Example 2 |
| --- | --- | --- |
| 0 weeks | 100% | 100% |
| 3 weeks | 85% | 135% |
| 6 weeks | 15% | 97% |
| 9 weeks | 9% | 86% |

The toothpaste composition containing 0.20-percent manganese chloride is about 9.5 times more stable than the corresponding toothpaste having no manganese ions present. Calcium and magnesium ions also stabilize the toothpaste.

The above experiments clearly show the impressive stabilizing and activating characteristics of the metal ions herein claimed.

The following specific examples are further illustrative of the nature of the present invention, but it is understood that the invention is not limited thereto.

EXAMPLE 3

The following oral gel is prepared:

| | Percent by Weight |
| --- | --- |
| Glycerine | 10.00 |
| Sodium saccharin | 0.20 |
| Sodium benzoate | 0.50 |
| Irish moss | 2.00 |
| Sorbitol | 74.24 |
| Sodium N-lauroyl sarcosinate | 1.50 |
| Ethanol | 10.00 |
| Dextranase (Fungal origin, 200 units/mg. protein) | 0.01 |
| $MnCl_2.4H_2O$ | 0.25 |

EXAMPLE 4

The following mouthrinse concentrate is prepared:

| | Percent by Weight |
| --- | --- |
| Glycerine | 45.0 |
| Ethanol | 40.0 |
| Water (Deionized) | 8.8 |
| Tween 80 | 2.0 |
| Sodium saccharin | 2.0 |
| Dextranase (Beckman, activity 117 units/mg. protein) | 2.0 |
| $MnCl_2.4H_2O$ | 0.8 |
| Flavor | 0.3 |
| Dye | 0.3 |

Upon use the above concentrate is diluted 1 part mouthrinse concentrate to 3 parts water.

It will be apparent that various modifications may be made in the examples which fall within the scope of the invention.

What is claimed is:

1. A dental cream or gel comprising a carrier material, dextranase having an activity of about 20 to 400 units/mg. protein in amount of about 0.001 to about 5% by weight and a non-toxic compound which provides an effective amount of at least 0.001% of stabilizer/activator manganous metal ions said metal ions being provided from water-soluble salts selected from the group consisting of chlorides, sulfates and nitrates, namely manganous chloride, manganous sulfate and manganous nitrate, said metal ions being effective to stabilize said dextranase and activate its dextranase activity.

2. The dental cream or gel of claim 1 in which the dextranase has an activity of about 90 to about 400 units/mg. protein.

3. The dental cream or gel of claim 2 wherein said carrier material includes about 20 to about 75% by weight of a liquid vehicle and about 20 to about 75% by weight of a polishing agent.

4. The dental cream or gel of claim 1 wherein said metal ions are provided from chloride salts.

* * * * *